US012725703B2

(12) United States Patent
Castillo et al.

(10) Patent No.: US 12,725,703 B2
(45) Date of Patent: Sep. 1, 2026

(54) CONTROL SYSTEMS AND METHODS FOR REMOTE AUDIOLOGISTS

(71) Applicant: GLOBALMEDIA GROUP, LLC, Scottsdale, AZ (US)

(72) Inventors: Met Castillo, Scottsdale, AZ (US); David Bosen, Chandler, AZ (US); Mateusz Urbanek, Phoenix, AZ (US)

(73) Assignee: GLOBALMED HOLDINGS, LLC, Scottsdale, AZ (US)

( * ) Notice: Subject to any disclaimer, the term of this patent is extended or adjusted under 35 U.S.C. 154(b) by 193 days.

(21) Appl. No.: 18/383,402

(22) Filed: Oct. 24, 2023

(65) Prior Publication Data

US 2024/0136061 A1 Apr. 25, 2024
US 2024/0233936 A9 Jul. 11, 2024

Related U.S. Application Data

(60) Provisional application No. 63/419,261, filed on Oct. 25, 2022.

(51) Int. Cl.
*G16H 40/67* (2018.01)
*A61B 5/12* (2006.01)

(52) U.S. Cl.
CPC ............. *G16H 40/67* (2018.01); *A61B 5/123* (2013.01)

(58) Field of Classification Search
CPC ........ G16H 40/67; G16H 10/60; A61B 5/123; A61B 5/0002
USPC .............................................................. 705/2
See application file for complete search history.

(56) References Cited

U.S. PATENT DOCUMENTS

| | | | | |
|---|---|---|---|---|
| 2013/0177176 | A1* | 7/2013 | Vumbaco | H04R 3/00 381/123 |
| 2019/0141458 | A1* | 5/2019 | Wendt | H04R 25/70 |
| 2021/0329393 | A1* | 10/2021 | Swetlitz | A61B 5/7475 |
| 2023/0300532 | A1* | 9/2023 | Spittle | G06F 3/165 381/1 |

FOREIGN PATENT DOCUMENTS

WO WO-2005125277 A2 * 12/2005 ............. A61B 5/121

OTHER PUBLICATIONS

Danielle L. DiFabio, Robin O'Hagan, & Danielle Glista; A Scoping Review of Technology and Infrastructure Needs in the Delivery of Virtual Hearing Aid Services; American Journal of Audiology; vol. 3, pp. 411-426, Jun. 2022 (Year: 2022).*

* cited by examiner

*Primary Examiner* — Alaaeldin M. Elshaer
*Assistant Examiner* — Teresa S Williams
(74) *Attorney, Agent, or Firm* — SNELL & WILMER L.L.P.

(57) ABSTRACT

Systems and methods for facilitating an auditory exam of a patient can comprise auditorily coupling an audiologist device in a remote location to test headphones and virtual health practitioner headphones through a test device. The systems and methods can include switching, via an A/B switch device, between the examination mode and a pre-examination mode and vice versa.

19 Claims, 6 Drawing Sheets

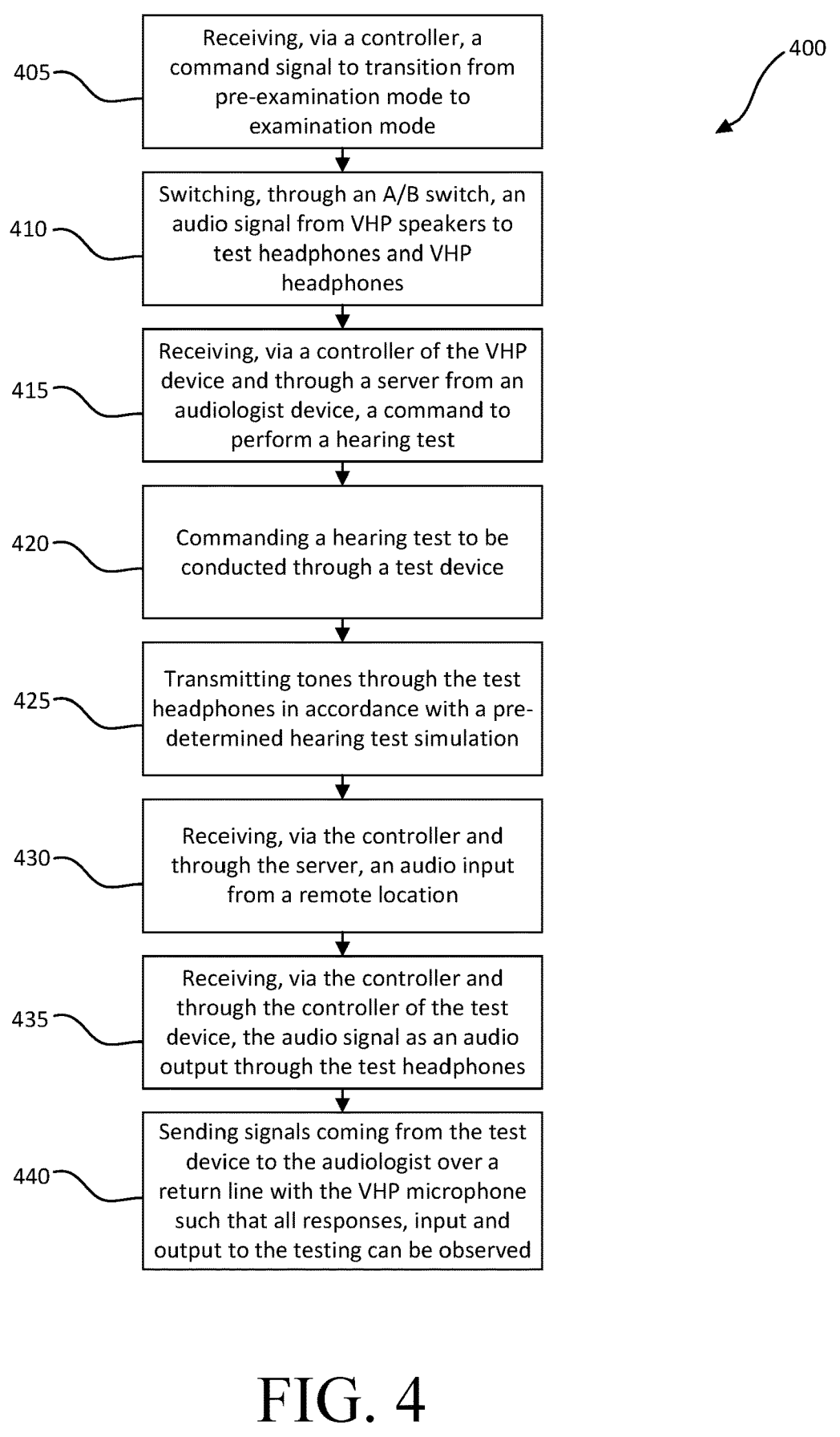

400

405 Receiving, via a controller, a command signal to transition from pre-examination mode to examination mode 410 Switching, through an A/B switch, an audio signal from VHP speakers to test headphones and VHP headphones 415 Receiving, via a controller of the VHP device and through a server from an audiologist device, a command to perform a hearing test 420 Commanding a hearing test to be conducted through a test device 425 Transmitting tones through the test headphones in accordance with a pre-determined hearing test simulation 430 Receiving, via the controller and through the server, an audio input from a remote location 435 Receiving, via the controller and through the controller of the test device, the audio signal as an audio output through the test headphones 440 Sending signals coming from the test device to the audiologist over a return line with the VHP microphone such that all responses, input and output to the testing can be observed

FIG. 4

CONTROL SYSTEMS AND METHODS FOR REMOTE AUDIOLOGISTS

CROSS-REFERENCE TO RELATED APPLICATIONS

This application claims priority to, and the benefit of, Provisional Patent Application No. 63/419,261, filed Oct. 25, 2022 and titled "CONTROL SYSTEMS AND METHODS FOR REMOTE AUDIOLOGIST," which is incorporated by reference herein in its entirety for all purposes

FIELD

The present disclosure generally relates to control systems and methods for remote audiologists, and more specifically to control of audio examination at a local location by an audiologist in a remote location.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may be inventions.

Typical audiology methods and systems facilitate communication between an audiologist in remote location with a patient in a local location. Typically, the audiologist can communicate with the patient and a Virtual-Health Practitioner ("VHP") or the like helping to facilitate the patient visit; however, the remote audiologist typically has to ask the VHP to control a testing device locally. The testing device is an independent device typically controlled and monitored in person, resulting in a delay, as well as inconvenience, for the audiologist.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

FIG. 4 illustrates a view of a process performed by the system of FIG. 1, in accordance with various embodiments.

DETAILED DESCRIPTION

Figure 1:
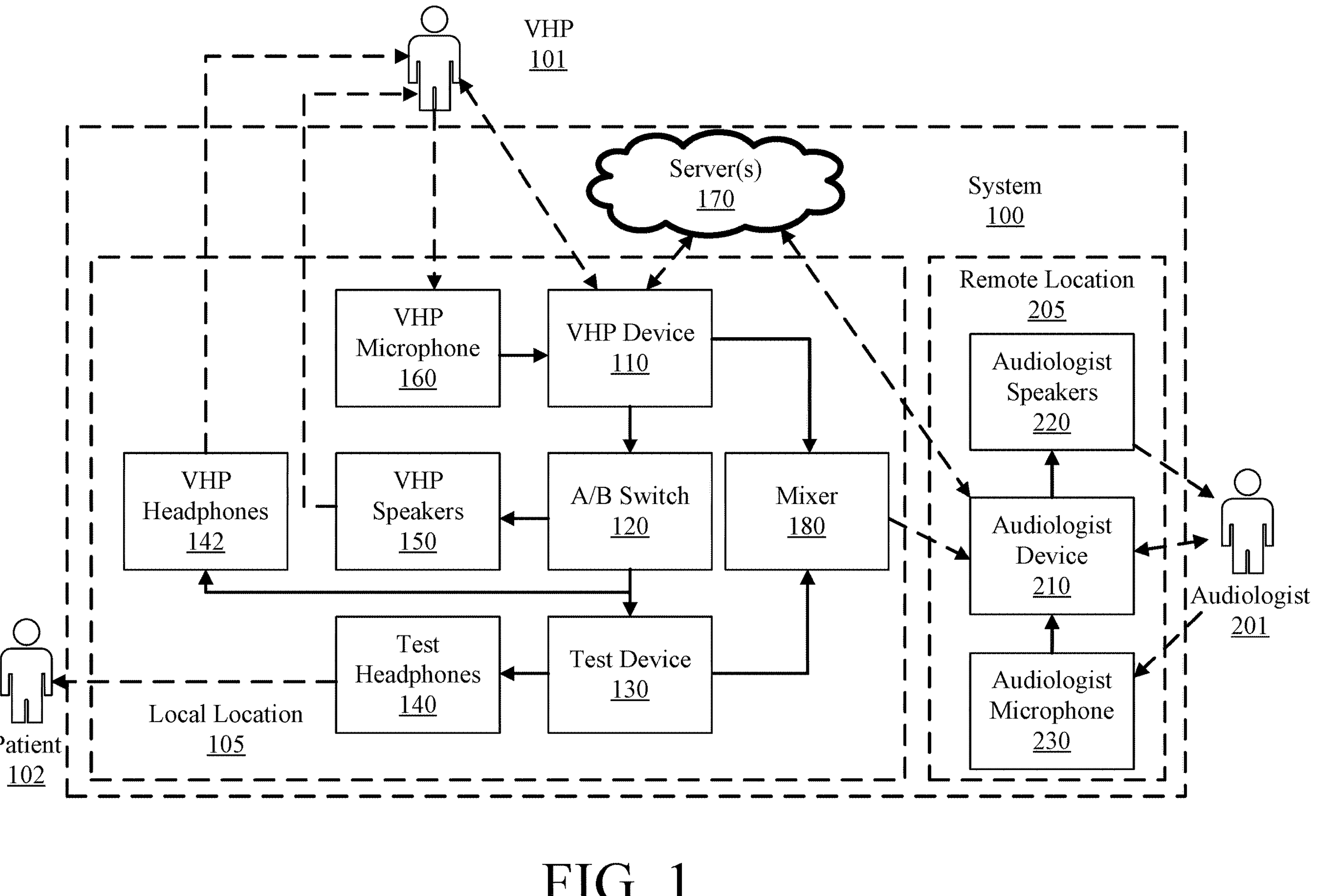
FIG. 1 illustrates a system for facilitating remote control over a telemedicine hearing test, in accordance with various embodiments.

The detailed description of exemplary embodiments herein refers to the accompanying drawings, which show exemplary embodiments by way of illustration and their best mode. While these exemplary embodiments are described in sufficient detail to enable those skilled in the art to practice the disclosures, it should be understood that other embodiments may be realized and that logical, chemical, and mechanical changes may be made without departing from the spirit and scope of the disclosures. Thus, the detailed description herein is presented for purposes of illustration only and not of limitation. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

Systems, methods, and computer program products are provided. In the detailed description herein, references to "various embodiments," "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Systems and process flows depicted are merely embodiments and are not intended to limit the scope of the disclosure. For example, the steps recited in any of the method or process descriptions may be executed in any suitable order and are not limited to the order presented. It will be appreciated that the following description makes appropriate references not only to the steps and user interface elements, but also to the various system components. It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below. Unless otherwise specifically noted, articles depicted in the drawings are not necessarily drawn to scale.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

These computer program instructions may be loaded onto a general-purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

In various embodiments, software may be stored in a computer program and loaded into a computer system using a removable storage drive, hard disk drive, or communications interface. The control logic (software), when executed by the processor, causes the processor to perform the functions of various embodiments as described herein. In various embodiments, hardware components may take the form of application specific integrated circuits (ASICs). Implementation of the hardware state machine so as to perform the functions described herein will be apparent to persons skilled in the relevant art(s).

As will be appreciated by one of ordinary skill in the art, the system may be embodied as a customization of an existing system, an add-on, a processing apparatus executing upgraded software, a stand-alone system, a distributed system, a method, a data processing system, a device for data processing, and/or a computer program. Accordingly, any portion of the system or a module may take the form of a processing apparatus executing code, an internet-based embodiment, an entirely hardware embodiment, or an embodiment combining aspects of the internet, software, and hardware. Furthermore, the system may take the form of a computer program on a computer-readable storage medium having computer-readable program code means embodied in the storage medium. Any suitable computer-readable storage medium may be utilized, including solid state storage, optical storage devices, magnetic storage devices, and/or the like.

Exemplary systems and methods may be described herein in terms of functional block components, screen shots, optional selections, and various processing steps. It should be appreciated that such functional blocks may be realized by any number of hardware and/or software components configured to perform the specified functions. For example, the system may employ various integrated circuit components, e.g., memory elements, processing elements, logic elements, and the like, which may carry out a variety of functions under the control of one or more microprocessors or other control devices. Similarly, the software elements of the system may be implemented with any programming or scripting language such as C, C++, C #, JAVA, JAVASCRIPT, JAVASCRIPT Object Notation (JSON), VBScript, Macromedia COLD FUSION, COBOL, MICROSOFT company's Active Server Pages, assembly, PERL, PHP, PYTHON, Visual Basic, SQL Stored Procedures, PL/SQL, or any UNIX shell script with the various algorithms being implemented with any combination of data structures, objects, processes, routines or other programming elements. Further, it should be noted that the system may employ any number of conventional techniques for data transmission, signaling, data processing, network control, Internet protocols and the like. Still further, the system could be used to detect or prevent use issues with a client-side scripting language, such as JAVASCRIPT, VBScript, or the like.

Exemplary systems and methods may be described herein with reference to screen shots, block diagrams and flowchart illustrations of methods, apparatus, and computer program according to various embodiments. It will be understood that each functional block of the block diagrams and the flowchart illustrations, and combinations of functional blocks in the block diagrams and flowchart illustrations, respectively, can be implemented by computer program instructions.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions.

For the sake of brevity, conventional data networking, application development, and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system or methods associated therewith.

Disclosed herein are remote audio testing systems and methods. The systems and methods disclosed herein facilitate control of audio channels.

In various embodiments, and with reference to FIG. 1, a system 100 for remote controlling of telehealth hearing test by an audiologist 201 (e.g., a remote tele-health testing control system) is illustrated. System 100 facilitates an audiologist 201 viewing and controlling a hearing test remotely without significant degradation, lag, and/or delay. System 100 may comprise a VHP device 110, a test device 130, VHP microphone 160, VHP speakers 150, test headphones 140 (e.g., test speaker headphones), VHP headphones 142, an A/B switch device 120, and/or an audio mixer 180 disposed in a local location 105; and an audiologist device 210, audiologist microphone 230, and audiologist speakers 220 disposed in a remote location 205. In various embodiments, a local location 105 is greater than 0.5 miles (0.8 km), or greater than 1 mile (1.6 km), or greater than 10 miles (16 km). However, the present disclosure is not limited in this regard. For example, a remote location can be greater than 1,000 s of miles (1,600 of kilometers) away and still be within the scope of this disclosure. System 100 may be utilized by an audiologist 201 utilizing the internet and communicating through a network, such as one or more servers 170 (e.g., eNcounter® exchange such as that sold by GlobalMedia Group, LLC, headquartered in Scottsdale, AZ), or any other telemedicine network or platform to control the test device 130 during a hearing examination, as well as to communicate with the VHP 101 and patient 102 prior to the hearing examination, in accordance with various embodiments as described further herein.

An audio mixer 180 is then used to mix the audio from the VHP microphone 160 and the test device 130 to the audiologist device 210. The audio mixer 180 can be a physical device or the audio mixer 180, the audio mixer 180 can be internal to the VHP device 110, or the audio mixer 180 can be performed by one or more processors on the VHP device. The present disclosure is not limited in this regard. In other example embodiments, the mixer could be located on the VHP device 110 directly.

In various embodiments, the audio mixer 180 can comprise an analog audio mixer, a powered analog audio mixer, a digital audio mixer, or the like. The present disclosure is not limited in this regard. In various embodiments, during operation of the system 100, the audio mixer 180 can be configured to receive a first audio line (e.g., from a VHP microphone 160) and a second audio line (e.g., from the test device 130), mix the first audio line and the second audio line, and transmit a mixed audio signal to the audiologist 201 (e.g., by the VHP device 110, through the one or more servers 170, through the audiologist device 210, and out the audiologist speakers 220). In various embodiments, the audio mixer 180 can be configured to provide a greater strength audio signal corresponding to the test device 130 (e.g., tones or the like). However, the present disclosure is not limited in this regard, and any type of mixing by the audio mixer 180 is within the scope of this disclosure.

In various embodiments, the test device 130 comprises a hearing test device, such as a Madsen® Astera 2 Clinical Audiometer sold by the company Natus® based in Madison, WI. Although described herein as comprising the Madsen® Astera 2 Clinical Audiometer, the present disclosure is not limited in this regard. For example, an audiologist device configured to generate a sequence of audio tones to test headphones 140 is within the scope of this disclosure.

In various embodiments, the audiologist 201 may desire to perform a hearing exam on a patient 102 remotely with the help of a VHP 101 via the system 100 (e.g., a telemedicine hearing examination). In performing the exam, it can be beneficial for the audiologist 201 to control the test device 130 during the examination to facilitate a smoother, more efficient, audiology examinations. This can be achieved by the VHP 101 transferring control of the VHP device 110 to the audiologist 201 (e.g., by the audiologist device 210 and through the one or more servers 170) in order for the audiologist 201 to engage the proper sequence to begin the test. However, prior to the examination, it may be desirable for the audiologist 201 to communicate with the VHP 101 and/or the patient 102 auditorily through a speaker that not associated with a hearing exam. In this regard, as described further herein, the system 100 facilitates alternating between various modes of communication to facilitate a tele-medicine health visit for a hearing examination or the like, in accordance with various embodiments. Stated another way, disclosed herein is the system 100 and processes for performing the examination remotely, in accordance with various embodiments.

In various embodiments, the VHP device 110 is operably coupled to an A/B switch device 120. In various embodiments, the A/B switch device 120 is coupled via electrical harness, however, the present disclosure is not limited in this regard. For example, in various embodiments, the A/B switch device could be contained directly on the VHP device 110, the A/B switch device 120 could be independent and separate from the VHP device, or the like. The present disclosure is not limited in this regard.

In various embodiments, the A/B switch device 120 is in operable communication with VHP speakers 150 and the test device 130. In this regard, the VHP device 110 is configured to alternate an electrical signal between the VHP speakers 150 and the test device 130 as described further herein. In various embodiments, the VHP device 110 can be controlled through a network (e.g., one or more servers 170) via the audiologist device 210. This is achieved by the VHP 101 giving access and control to the audiologist 201 to command the VHP device 110. For example, the audiologist 201 can be capable of controlling the test environment remotely, as described further herein. Stated another way, the audiologist 201 can control various inputs of the test device 130 by the audiologist device 210 and through the VHP device 110, in accordance with various embodiments.

In various embodiments, devices 110, 130, 210 may comprise various hardware, software, and/or database components configured to enable each device (e.g., VHP device 110, test device 130, and/or audiologist device 210) to participate in system 100 and allow the audiologist 201 to view, control, and conduct a hearing examination from prior to the examination until after the examination without the VHP 101 controlling the hearing test locally. For example, each device (e.g., VHP device 110, test device 130, and/or audiologist device 210) may be computer based, and may comprise a processor, a tangible non-transitory computer-readable memory, along with other suitable system software and hardware components. In various embodiments, audiologist device 210 and VHP device 110 each comprise a network interface (e.g., via a network such as a local area network, a wide area network, etc. via TCP/IP protocol). In this regard, the audiologist device 210 and the VHP device 110 can communicate via their own network interface through the one or more servers 170. Instructions stored on the tangible non-transitory memory for each device (e.g., VHP device 110, test device 130, and/or audiologist device 210) may allow each device (e.g., VHP device 110, test device 130, and/or audiologist device 210) to perform various functions, as described herein. The processor may include any logic device such as one or more of a central processing unit (CPU), an accelerated processing unit (APU), a digital signal processor (DSP), a field programmable gate array (FPGA), an application specific integrated circuit (ASIC), or the like.

Figure 2:
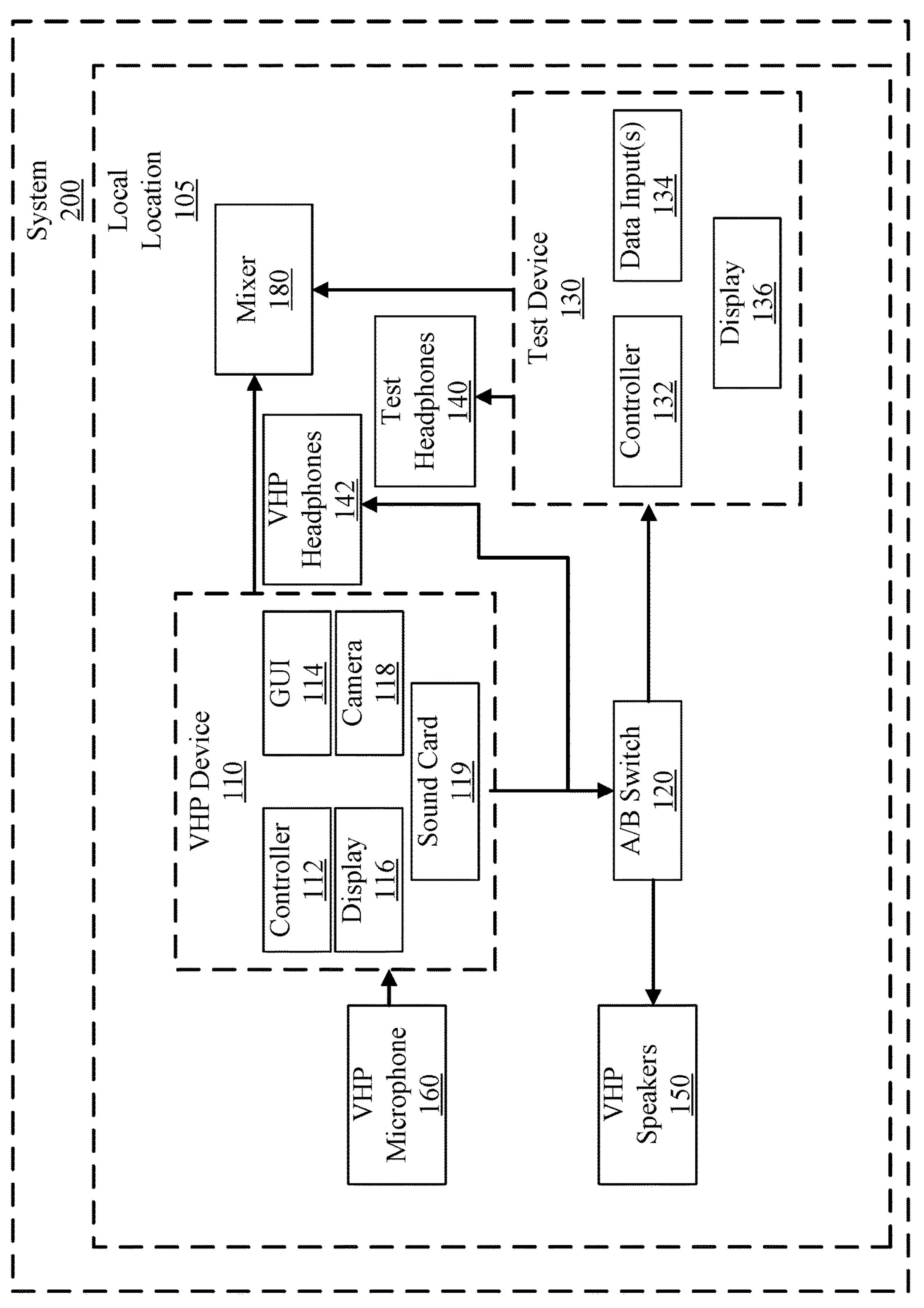
FIG. 2 illustrates a detail view of a local location system for facilitating remote control over a telemedicine hearing test, in accordance with various embodiments.

Referring now to FIG. 2, a detailed schematic view of a local system 200 (i.e., a system in the local location 105 from FIG. 1) for facilitating remote telemedicine testing for a hearing examination is illustrated, in accordance with various embodiments. In various embodiments, the VHP device 110 further comprises a controller 112 in electronic communication with the audiologist device 210 through the one or more servers 170 from FIG. 1, in accordance with various embodiments. For example, the controller 112 of the VHP device 110 is configured to receive input signals and send output signals to the audiologist device 210 (e.g., through the one or more servers 170 as shown in FIG. 1), in accordance with various embodiments. The VHP device 110 can be further configured to communicate visually (e.g., by a graphical user interface ("GUI") 114, a display 116, and a camera 118) with the audiologist device 210 through the one or more servers 170.

In various embodiments, the VHP device 110 is also configured to contain a sound card 119 to amplify the audio levels of the VHP microphone 160. In various embodiments, the sound card can comprise a motherboard sound chip, an expansion sound card, or an external sound adapter. The present disclosure is not limited in this regard, and any sound card 119 that is configured to amplify audio levels of the VHP microphone 160 is within the scope of this disclosure. In various embodiments, amplification of the VHP microphone 160 can help facilitate a smooth mixing of the VHP microphone and tones generated from the test device 130 during operation. In this regard, typical sound levels for the VHP microphone 160 could be insufficient for an audiologist to hear the VHP 101 during an audio examination, in accordance with various embodiments. In various embodiments, the sound card 119 is a separate physical device from the VHP device 110. In various embodiments, the sound card 119 is internal to the VHP device 110. The present disclosure is not limited in this regard.

In various embodiments, the controller 112 is in electronic communication with the VHP microphone 160 and the A/B switch device 120. In various embodiments, during remote testing, the VHP 101 can communicate with the audiologist 201 through the VHP microphone 160 regardless of an operating mode of the system 200. For example, in a pre-examination mode, the VHP 101 and the patient 102 can communicate through the VHP microphone 160 of the system 200 and an output signal can be sent to the audiologist device 210 through the one or more servers 170. Similarly, during a hearing examination mode, the VHP 101 can communicate to the audiologist 201 via the VHP microphone 160, through the controller 112 of the VHP device 110, which transmits an output signal through the one or more servers 170 to the audiologist device 210, which outputs the signal through the audiologist speakers 220 from FIG. 1, in accordance with various embodiments. In various embodiments, in the "pre-examination mode," the patient 102 does not have the test headphones 140 on, and/or the examination is being prepared for. In various embodiments, in the "examination mode" the patient 102 has the test headphones 140 on and a hearing test is being performed through test device 130 as described further herein.

In various embodiments, the test device 130 can comprise one or more data inputs 134. The one or more data inputs 134 can physical data inputs, digital data inputs, or the like. The present disclosure is not limited in this regard. In various embodiments, the one or more data inputs 134 are configured to control various parameters of an audio output during a hearing exam. For example, the one or more data inputs 134 can control a volume during the hearing examination, a sequence of tones during the hearing exam, a type of tones output during the hearing examination, or the like. The present disclosure is not limited in this regard.

In various embodiments, the test device 130 can comprise a display 136. In this regard, various parameters that have been set for the test device 130 can be visually provided to a user through the display 136, in accordance with various embodiments. Although illustrated as including a display 136, the present disclosure is not limited in this regard. For example, the test device 130 may not include a display 136 and would still be within the scope of this disclosure.

Figure 3:
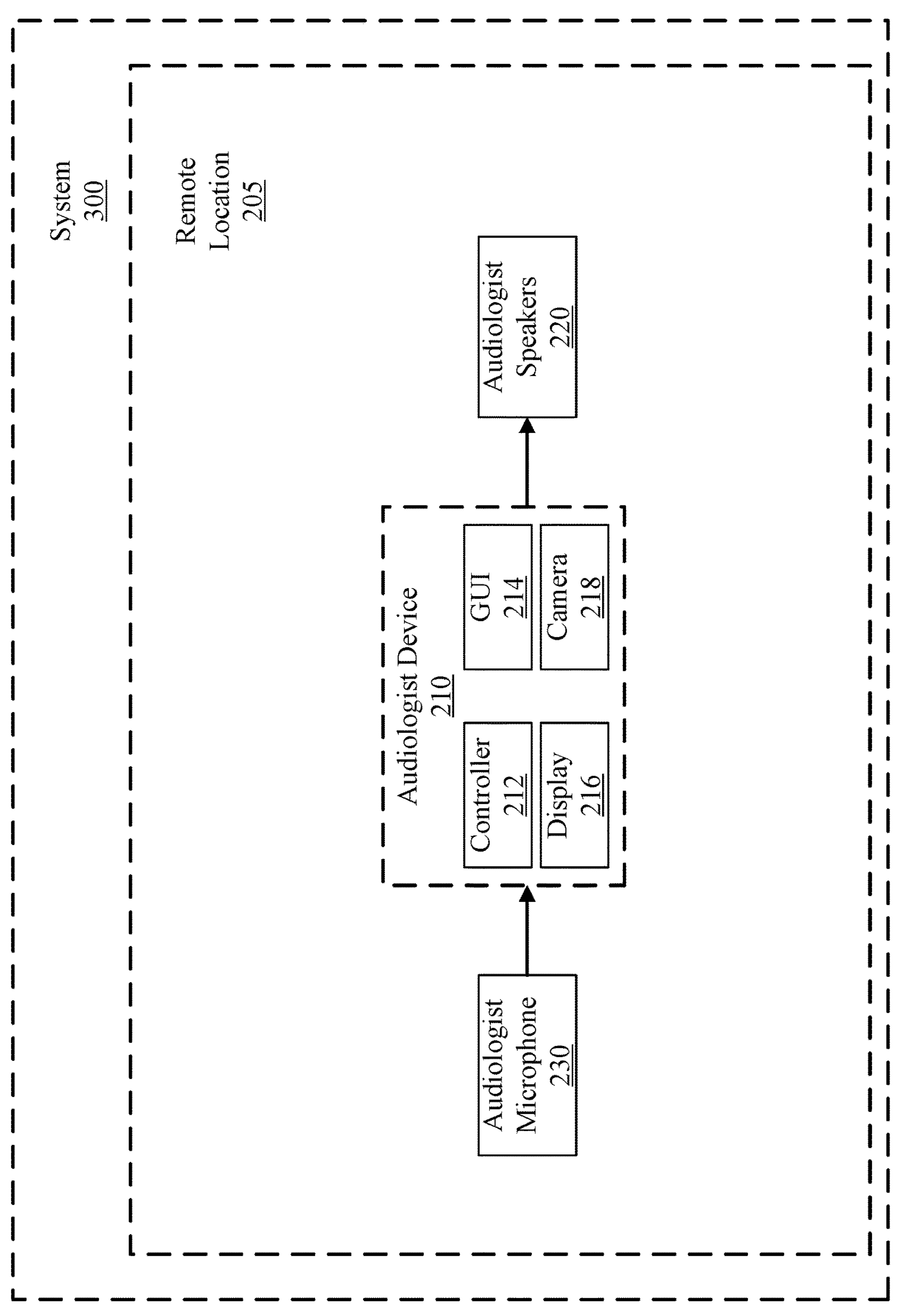
FIG. 3 illustrates a detail view of a remote location system for facilitating remote control over a telemedicine hearing test, in accordance with various embodiments.
Figure 5:
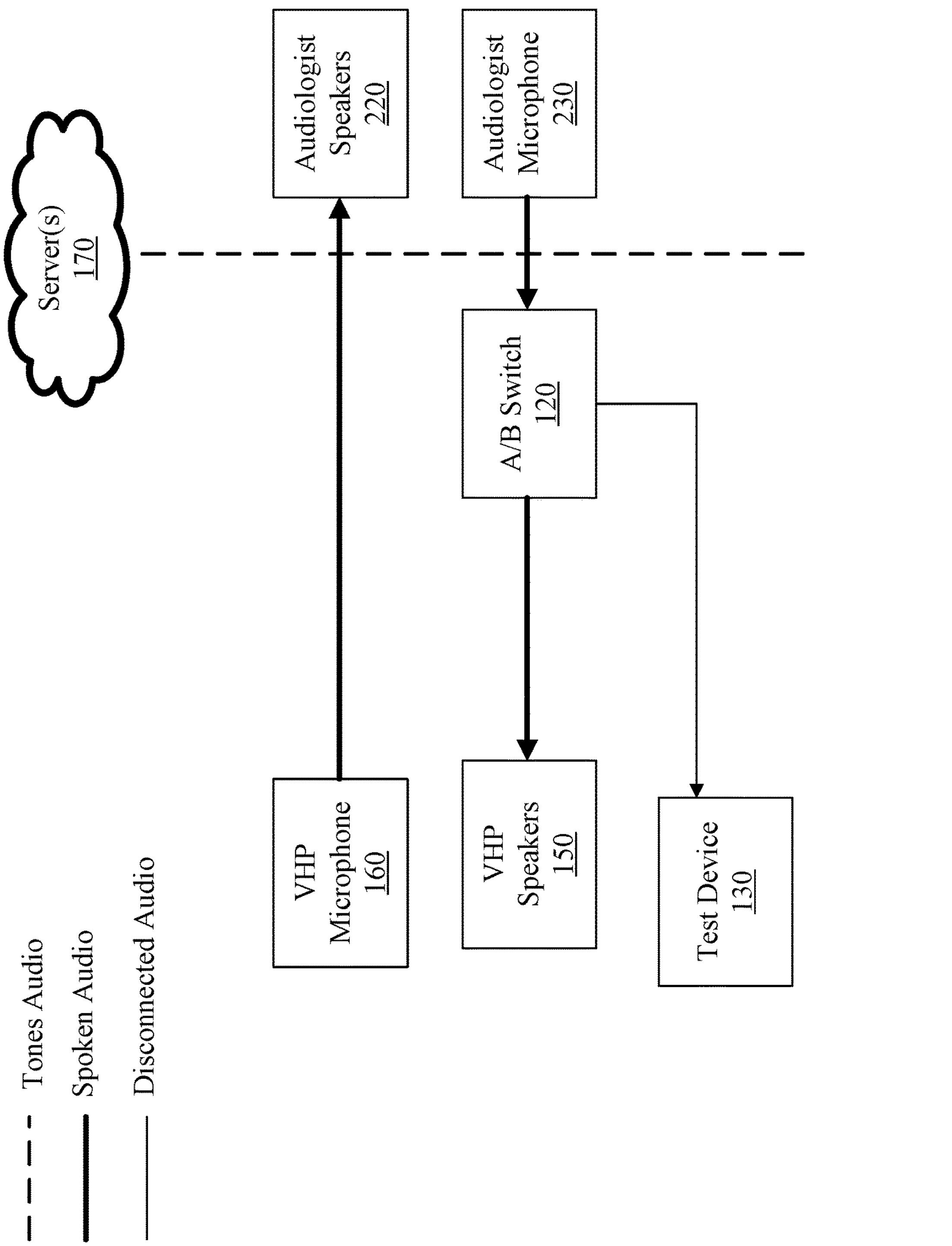
FIG. 5 illustrates a schematic view of a portion of the system from FIG. 1 in a pre-examination mode, in accordance with various embodiments.

Referring now to FIG. 3, a detailed schematic view of a remote system 300 (i.e., a system in the remote location 205 from FIG. 1) for facilitating remote telemedicine testing for a hearing examination is illustrated, in accordance with various embodiments. In various embodiments, the audiologist device 210 further comprises a controller 212 in electronic communication with the VHP device 110 through the one or more servers 170 from FIG. 1, in accordance with various embodiments. For example, as described further herein, the controller 212 of the audiologist device 210 is configured to receive input signals and send output signals to the VHP device 110 through the one or more servers 170 as shown in FIG. 1, in accordance with various embodiments. In addition, the audiologist device 210 is configured to communicate visually by a display 216 and camera 218 with the VHP device 110 through the one or more servers 170.

In various embodiments, the audiologist device 210 can comprise a graphical user interface ("GUI") 214. The GUI 214 can enable the audiologist 201 from FIG. 1 to control the hearing test in accordance with various embodiments. For example, the GUI 214 can include data inputs that correspond to physical inputs (e.g., the one or more data inputs 134 of the test device 130 as shown in FIG. 3) that is disposed in the local location 105 from FIG. 1. Accordingly, the audiologist 201 can control the test device 130 remotely through by the audiologist device 210 through the one or more servers 170 (and/or a TCP/IP protocol) and the VHP device 110, in accordance with various embodiments.

In various embodiments, and with combined reference now to FIGS. 1-6, an audiologist 201 can transition from the pre-examination mode (FIG. 5) to the examination mode (FIG. 6) in accordance with the process 400 (FIG. 4). For example, the process 400 comprises receiving, via a controller 112 of the VHP device 110 and through one or more servers 170 from an audiologist device 210, a command signal to transition from a pre-examination mode (FIG. 5) to an examination mode (FIG. 6) (step 405).

In various embodiments, in response to receiving the command signal in step 405, the process 400 further comprises switching, through an A/B switch device 120, an audio output signal from VHP speakers 150 to test headphones 140 and VHP headphones 142 (step 410). With brief reference to FIG. 5, in the examination mode, the audio output of the A/B switch device 120 can be auditorily coupled to the test headphones 140 and the VHP headphones 142 through the test device 130 (or through the controller 132 of the test device 130) to the test headphones 140 and the VHP headphones 142. In this regard, in response to the audiologist 201 speaking through the audiologist microphone, the spoken audio can be transmitted to the test headphones 140 and the VHP headphones 142 to allow the audiologist 201 to communicate with the patient 102 and the VHP 101 during the examination mode, in accordance with various embodiments.

In various embodiments, in the examination mode, the test device 130 can be auditorily coupled to the test headphones 140 (i.e., in a typical manner), and auditorily coupled to the VHP device 110. In various embodiments, by auditorily coupling the test device 130 to the VHP device 110, the tone data generated from the test device 130 can be forwarded through the VHP device 110, mixed with any spoken audio from the VHP microphone 160 (e.g., via audio mixer 180), and transmitted (e.g., via the one or more servers 170 or TCP/IP protocol) to the audiologist speakers 220.

In various embodiments, in response to switching from the pre-examination mode to the examination mode, the controller 112 can be operably coupled to the controller 132 (e.g., through a second of the A/B switch device 120, or similar device). However, the present disclosure is not limited in this regard. For example, the controller 112 can be electronically coupled to the controller 132 directly and still be within the scope of this disclosure. Yet, by coupling the command line through the A/B switch device 120, as well as the audio line through the A/B switch device 120, the system 200 can ensure that the test device 130 is only operable through the controller 112 during a tele-medicine operation. In this regard, if the test device 130 were to be used by a local audiologist, the local audiologist could use the test device 130 directly without use of the VHP device 110, in accordance with various embodiments.

Figure 6:
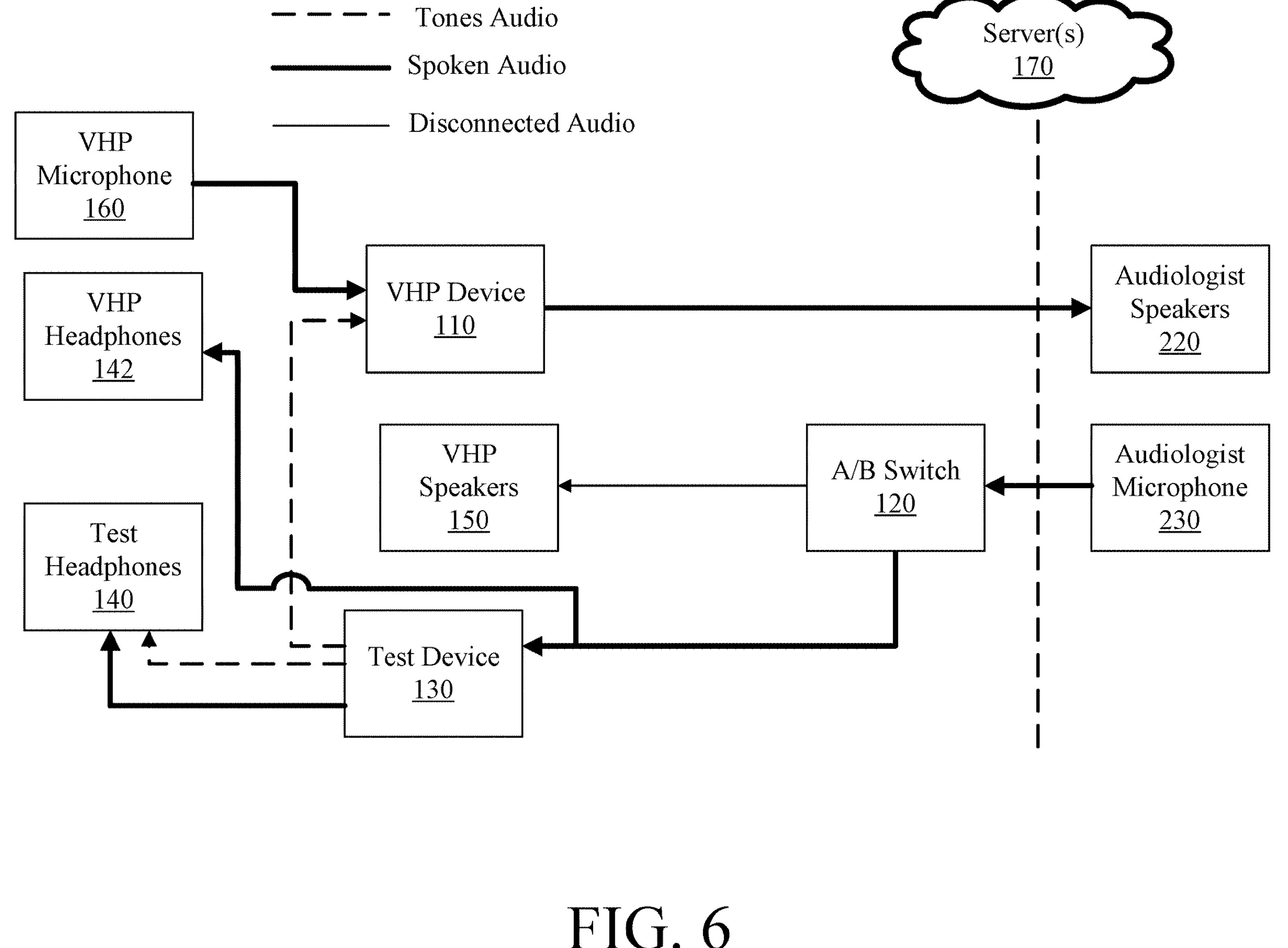
FIG. 6 illustrates a schematic view of a portion of the system from FIG. 1 in an examination mode, in accordance with various embodiments.

In various embodiments, the process 400 further comprises receiving, via a controller 112 of the VHP device 110 and through one or more servers 170 from an audiologist device 210, a command to perform a hearing test (step 415). In response to receiving the command in step 415, the controller 112 can command a hearing test to be conducted through a test device 130 (step 420). In various embodiments, in response to receiving the command from step 420, the test device 130 can transmit tones through the test headphones 140 (e.g., as illustrated in FIG. 6) in accordance with a hearing test simulation (step 425). In this regard, the test device 130 can conduct the hearing test based on receiving a command from a remote location 205, in accordance with various embodiments. In various embodiments, the hearing test simulation can include a pre-determined sequence of tones, a controlled sequence of tones (e.g., controlled by the audiologist 201 through the audiologist device 210), or the like. The present disclosure is not limited in this regard.

In various embodiments, the process 400 further comprises receiving, via the controller 112 and through the one or more servers 170, an audio input from a remote location 205 (e.g., from the audiologist microphone 230) (step 430). In various embodiments, the process 400 further comprises receiving, via the controller 112 and through the controller 132 of the test device 130, the audio signal as an audio output through the test headphones 140 (step 435). Signals coming from the test device 130 can also be combined by the audio mixer 180 and sent back to the audiologist 201 over a return line with the VHP microphone 160 such that all responses, input and output to the testing can be observed (step 440). In this regard, the audiologist 201 can communicate with the patient 102 during the examination mode as shown in FIG. 6, in accordance with various embodiments.

Benefits, other advantages, and solutions to problems have been described herein regarding specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosures.

The scope of the disclosures is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods, and apparatus are provided herein. In the detailed description herein, references to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

What is claimed is:

1. A test system for use by a virtual-health practitioner ("VHP"), the test system comprising:

a hearing test device including one or more test headphones, the one or more test headphones operably coupled to a controller of the hearing test device, the hearing test device configured to facilitate a hearing test of a patient;

a VHP speaker and VHP headphones;

a VHP device configured to facilitate a virtual-health visit and comprising a controller; and an A/B switch auditorily coupled to the VHP speaker, the hearing test device, and the VHP device, the A/B switch configured to switch the test system from a pre-examination mode to an examination mode, wherein, during operation of the test system, the VHP device is configured to communicate with the audiologist through a VHP microphone regardless of an operating mode of the test system, wherein switching from the pre-examination mode to the examination mode comprises placing the controller of the hearing test device in operable communication with the controller of the VHP device through the A/B switch, wherein, in response to transitioning from the pre-examination mode to the examination mode, the A/B switch switches an audio output signal from the VHP speaker to the one or more test headphones and the VHP headphones, wherein, when in the examination mode, the controller of the VHP device commands the controller of the hearing test device to conduct the hearing test of the patient, and wherein an audio output of the A/B switch is auditorily coupled to the one or more test headphones and the VHP headphones through the hearing test device so that spoken audio from an audiologist microphone is transmitted to the patient and the VHP through the one or more test headphones and the VHP headphones.

2. The test system of claim 1, further comprising an audio mixer auditorily coupled to the hearing test device and the VHP device.

3. The test system of claim 2, wherein:

the audio mixer is configured to receive a first audio input from the hearing test device and a second audio input from the VHP microphone and form a mixed audio output, and transmit the mixed audio output to an audiologist device through one or more servers.

4. The test system of claim 2, wherein the audio mixer is disposed within the VHP device.

5. The test system of claim 1, wherein:

the A/B switch further comprises a first data input and a second data input, responsive to engaging the first data input, the auditory output from the A/B switch transitions from the hearing test device to the VHP speaker, and responsive to engaging the second data input, the auditory output transitions from the VHP speaker to the hearing test device.

6. The test system of claim 1, wherein the hearing test device is auditorily coupled to the one or more test headphones and the VHP device.

7. The test system of claim 6, wherein the VHP device comprises a VHP microphone and a VHP controller, the VHP controller configured to:

receive a set of tones from the hearing test device;

receive audio data from the VHP microphone;

mix the set of tones and the audio data to form a single audio output; and transmit the single audio output through one or more servers to an audiologist speaker.

8. The test system of claim 7, further comprising the audiologist speaker, wherein the audiologist speaker is disposed in a remote location relative to the VHP microphone.

9. A method for conducting a remote hearing test, the method comprising:

switching, by an A/B switch, a hearing test system from a pre-examination mode to an examination mode, wherein in response to the switching the hearing test system from the pre-examination mode to the examination mode, a remote microphone is auditorily coupled to test headphones of the hearing test system, the hearing test system disposed in a local location, wherein, during operation of the test system, a virtual-health practitioner ("VHP") device is configured to communicate with the audiologist through a VHP microphone regardless of an operating mode of the test system, wherein switching from the pre-examination mode to the examination mode comprises placing a controller of the hearing test device in operable communication with a controller of the VHP device through the A/B switch, wherein, in response to transitioning from the pre-examination mode to the examination mode, the A/B switch switches an audio output signal from a VHP speaker to the test headphones and VHP headphones, wherein, when in the examination mode, the controller of the VHP device commands the controller of the hearing test device to conduct the remote hearing test of the patient, and wherein an audio output of the A/B switch is auditorily coupled to the test headphones and the VHP headphones through the hearing test device so that spoken audio from an audiologist microphone is transmitted to the patient and the VHP through the test headphones and the VHP headphones; and initiating, by one or more processors, a hearing test, wherein in response to initiating the hearing test, a set of tones are output through the test headphones.

10. The method of claim 9, wherein in response to initiating the hearing test, the set of tones are simultaneously output through a remote speaker.

11. The method of claim 10, wherein the remote speaker and the remote microphone are physically decoupled from the VHP device.

12. The method of claim 10, wherein the set of tones are transmitted through a mixer.

13. The method of claim 12, further comprising:

receiving audio data through a local microphone disposed in the local location; and transmitting the audio data through the mixer, and out the remote speaker, wherein an audio output corresponding to the audio data and the set of tones is output together from the remote speaker.

14. The method of claim 9, further comprising:

receiving, by the one or more processors, from the remote microphone, and through one of a server or a Transmission Control Protocol/Internet Protocol, audio data; and transmitting, by the one or more processors, audio corresponding to the audio data through the test headphones.

15. The method of claim 14, further comprising transmitting, by the one or more processors, an audio output corresponding to the audio data through the VHP headphones.

16. The method of claim 9, wherein in response to the switching the hearing test system from the pre-examination mode to the examination mode, a speaker disposed in the local location is auditorily de-coupled from the remote microphone.

17. An article of manufacture including a tangible, non-transitory computer-readable storage medium having instructions stored thereon that, in response to execution by one or more processors, cause the one or more processors to perform operations comprising:

switching, by the one or more processors, a hearing test system from a pre-examination mode to an examination mode, wherein in response to the switching the hearing test system from the pre-examination mode to the examination mode, a remote microphone is auditorily coupled to test headphones of the hearing test system, the hearing test system disposed in a local location, wherein, during operation of the test system, a virtual-health practitioner ("VHP") device is configured to communicate with the audiologist through a VHP microphone regardless of an operating mode of the test system, wherein switching from the pre-examination mode to the examination mode comprises placing a controller of the hearing test device in operable communication with a controller of the VHP device through the A/B switch, wherein, in response to transitioning from the pre-examination mode to the examination mode, the A/B switch switches an audio output signal from a VHP speaker to the test headphones and VHP headphones, wherein, when in the examination mode, the controller of the VHP device commands the controller of the hearing test device to conduct the remote hearing test of the patient, and wherein an audio output of the A/B switch is auditorily coupled to the test headphones and the VHP headphones through the hearing test device so that spoken audio from an audiologist microphone is transmitted to the patient and the VHP through the test headphones and the VHP headphones; and initiating, by the one or more processors, a hearing test, wherein in response to initiating the hearing test, a set of tones are output through the test headphones.

18. The article of manufacture of claim 17, wherein in response to initiating the hearing test, the set of tones are simultaneously output through a remote speaker.

19. The article of manufacture of claim 17, wherein in response to the switching the hearing test system from the pre-examination mode to the examination mode, a speaker disposed in the local location is auditorily de-coupled from the remote microphone.

* * * * *